(12) United States Patent
Dillard

(10) Patent No.: US 10,433,901 B2
(45) Date of Patent: Oct. 8, 2019

(54) METHOD FOR TREATMENT OF SLEEP APNEA BY VENTRAL ONLY ABLATION OF THE TONGUE

(71) Applicant: David G. Dillard, Atlanta, GA (US)

(72) Inventor: David G. Dillard, Atlanta, GA (US)

(*) Notice: Subject to any disclaimer, the term of this patent is extended or adjusted under 35 U.S.C. 154(b) by 65 days.

(21) Appl. No.: 15/417,461

(22) Filed: Jan. 27, 2017

(65) Prior Publication Data

US 2017/0135755 A1 May 18, 2017

Related U.S. Application Data

(62) Division of application No. 14/012,305, filed on Aug. 28, 2013, now Pat. No. 9,554,852.

(Continued)

(51) Int. Cl.
*A61B 18/14* (2006.01)
*A61B 18/18* (2006.01)
(Continued)

(52) U.S. Cl.
CPC ............ *A61B 18/1485* (2013.01); *A61B 1/24* (2013.01); *A61B 17/0218* (2013.01);
(Continued)

(58) Field of Classification Search
CPC ............ A61B 18/1485; A61B 17/0218; A61B 18/1477; A61B 2090/0817;
(Continued)

(56) References Cited

U.S. PATENT DOCUMENTS 4,606,346 A 8/1986 Berg et al.
5,139,510 A 8/1992 Goldsmith, III et al.
(Continued)

OTHER PUBLICATIONS

Ceylan, K., et al., First-choice treatment in mild to moderate obstructive sleep apnea: single-stage, multilevel, temperature-controlled radiofrequency tissue volume reduction or nasal continuous positive airway pressure, Arch Otolaryngol Head Neck Surg., Sep. 2009, pp. 915-919; vol. 135, No. 9.

(Continued)

*Primary Examiner* — Lynnsy M Summitt
*Assistant Examiner* — Tara Rose E Carter
(74) *Attorney, Agent, or Firm* — Morris, Manning & Martin, LLP; John R. Harris

(57) ABSTRACT

Apparatus and methods for ventral only ablation of the tongue, for use in treating sleep apnea and related breathing disorders. An RF ablation probe or wand is inserted in ventral surface of a patient's tongue in a superior plane along a longitudinal (i.e., anterior to posterior) axis of the tongue, to a predetermined depth. The wand is withdrawn, RF energy is applied, creating a lesion predominantly in the interior of the tongue in an anterior to posterior plane, thereby resulting in less scarring but appreciable movement of the posterior tongue base away from the posterior pharyngeal wall. Also disclosed is a tongue retractor device used for measuring the depth of wand insertion, lifting the tongue to expose the ventral surface of the tongue for the procedure, and providing a stop surface to inhibit further wand insertion.

22 Claims, 14 Drawing Sheets

Related U.S. Application Data

(60) Provisional application No. 61/695,860, filed on Aug. 31, 2012.

(51) Int. Cl.

| | | |
|---|---|---|
| *A61B 1/24* | (2006.01) | |
| *A61B 17/02* | (2006.01) | |
| *A61B 18/04* | (2006.01) | |
| *A61B 18/00* | (2006.01) | |
| *A61B 18/12* | (2006.01) | |
| *A61B 90/00* | (2016.01) | |
| *A61B 5/107* | (2006.01) | |
| *A61B 17/00* | (2006.01) | |
| *A61B 17/24* | (2006.01) | |

(52) U.S. Cl.
CPC ........ *A61B 18/042* (2013.01); *A61B 18/1477* (2013.01); *A61B 18/18* (2013.01); *A61B 5/1072* (2013.01); *A61B 2017/00814* (2013.01); *A61B 2017/248* (2013.01); *A61B 2018/00321* (2013.01); *A61B 2018/00434* (2013.01); *A61B 2018/00577* (2013.01); *A61B 2018/00583* (2013.01); *A61B 2018/126* (2013.01); *A61B 2018/1425* (2013.01); *A61B 2018/1472* (2013.01); *A61B 2090/0817* (2016.02)

(58) Field of Classification Search
CPC ............ A61B 2017/248; A61B 5/1072; A61B 2017/00814
See application file for complete search history.

(56) References Cited

U.S. PATENT DOCUMENTS

| | | | |
|---|---|---|---|
| 5,879,349 A * | 3/1999 | Edwards | A61B 5/04 606/45 |
| 6,231,571 B1 | 5/2001 | Ellman et al. | |
| 6,387,093 B1 | 5/2002 | Ellman et al. | |
| 6,726,684 B1 * | 4/2004 | Woloszko | A61B 18/148 606/32 |
| 6,746,447 B2 | 6/2004 | Davison et al. | |
| 7,090,672 B2 | 8/2006 | Underwood et al. | |
| 7,131,969 B1 | 11/2006 | Hovda et al. | |
| 7,491,200 B2 | 2/2009 | Underwood | |
| 7,824,395 B2 | 11/2010 | Chan et al. | |
| 7,992,566 B2 | 8/2011 | Pflueger et al. | |
| 8,290,582 B2 | 10/2012 | Lin et al. | |
| 8,381,735 B2 | 2/2013 | Buscemi et al. | |
| 2001/0051783 A1 * | 12/2001 | Edwards | A61B 18/1477 604/22 |

OTHER PUBLICATIONS

Eun Y.G., et al., Multilevel surgery in patients with rapid eye movement-related obstructive sleep apnea, Otolaryngol Head Neck Surg., Apr. 2009, pp. 536-541, vol. 140, No. 4.
Eun, Y.G., et al., Single-session radiofrequency tongue base reduction combined with uvulopalatopharyngoplasty for obstructive sleep apnea syndrome, Eur Arch Otorhinolaryngol., Dec. 2008, pp. 1495-1500, vol. 265, No. 12.
Farrar, J., et al., Radiofrequency ablation for the treatment of obstructive sleep apnea: a meta-analysis, Laryngoscope, Oct. 2008, pp. 1878-1883, vol. 118, No. 10.
Fernandez-Julian, E., et al., Randomized study comparing two tongue base surgeries for moderate to severe obstructive sleep apnea syndrome, Otolaryngol Head Neck Surg., Jun. 2009, pp. 917-923, vol. 140, No. 6.
Fischer, Y., et al., Multilevel temperature-controlled radiofrequency therapy of soft palate, base of tongue, and tonsils in adults with obstructive sleep apnea, Laryngoscope, Oct. 2003, pp. 1786-1791, vol. 113, No. 10.
Friedman, M., et al., Combined uvulopalatopharyngoplasty and radiofrequency tongue base reduction for treatment of obstructive sleep apnea/hypopnea syndrome, Otol H&N Surg, Dec. 2003, pp. 611-621, vol. 129, No. 6.
Friedman, M., et al., Minimally invasive single-stage multilevel treatment for obstructive sleep apnea/hypopnea syndrome, Laryngoscope, Oct. 2007, pp. 1859-1863, vol. 117, No. 10.
Gay, P., et al., Evaluation of positive airway pressure treatment for sleep related breathing disorders in adults, Sleep, 2006, pp. 381-401, vol. 29, No. 3.
Kezirian, E.J., et al., Incidence of complications in radiofrequency treatment of the upper airway, Laryngoscope, Jul. 2005, pp. 1298-1304, vol. 115, No. 7.
Li, K.K. et al. Temperature-controlled radiofrequency tongue base reduction for sleep-disordered breathing: Long-term outcomes, Otol H&N Surg, Sep. 2002, pp. 230-234, vol. 127, No. 3.
Lindberg, E., et al., CPAP treatment of a population-based sample—what are the benefits and the treatment compliance?, Sleep Medicine, 2006, pp. 553-560, V.
Maurer, J.T., Surgical treatment of obstructive sleep apnea: standard and emerging techniques, Current Opinion in Pulmonary Medicine, 2010, pp. 552-558, vol. 16, No. 6.
Nelson, L.M., et al., High energy single session radiofrequency tongue treatment in obstructive sleep apnea surgery, Otolaryngol Head Neck Surg., Dec. 2007, pp. 883-888, vol. 137, No. 6.
Pazos, G., et al., Complications of radiofrequency ablation in the treatment of sleep-disordered breathing, Otol H&N Surg, 2001, pp. 462-466, vol. 125, No. 5.
Powell, N.B., et al., Radiofrequency tongue base reduction in sleep-disordered breathing: A pilot study, Otol H&N Surg, 1999, pp. 656-664, vol. 120, No. 5.
Riley, R.W., et al., An adjunctive method of radiofrequency volumetric tissue reduction of the tongue for OSAS, Otol H&N Surg, 2003, pp. 37-42, vol. 129, No. 1.
Robinson, S., et al., Ultrasound-guided radiofrequency submucosal tongue-base excision for sleep apnoea: a preliminary report, Clin Otolaryngol, Feb. 2003, pp. 341-345, vol. 28, No. 4.
Richard, W., et al., Complications of hyoid suspension in the treatment of obstructive sleep apnea syndrome, Eur Arch Otorhinolaryngol., 2011, pp. 631-635, vol. 268, No. 4.
Steward, D.L, et al., A comparison of radiofrequency treatment schemes for obstructive sleep apnea syndrome, Otolaryngol Head Neck Surg., May 2004, pp. 579-585, vol. 130, No. 5.
Steward, D.L, Effectiveness of multilevel (tongue and palate) radiofrequency tissue ablation for patients with obstructive sleep apnea syndrome, Laryngoscope, Dec. 2004, pp. 2073-2084, vol. 114, No. 12.
Steward, D.L, et al., Multilevel temperature-controlled radiofrequency for obstructive sleep apnea: extended follow-up, Otolaryngol Head Neck Surg., 2005, pp. 630-635, vol. 132, No. 4.
Stuck, B.A., et al., Lesion formation in radiofrequency surgery of the tongue base, Laryngoscope, Sep. 2003, pp. 1572-1576, vol. 113, No. 9.
Stuck, B.A., et al., Volumetric tissue reduction in radiofrequency surgery of the tongue base, Otolaryngol Head Neck Surg., 2005, pp. 132-135, vol. 132, No. 1.
Toh, S.T., et al., Incidence of complications after temperature-controlled radiofrequency treatment for sleep-disordered breathing: a Singapore sleep centre experience, J Laryngol Otol, May 2008, pp. 490-494, vol. 122, No. 5.
Troell, R.J., Radiofrequency techniques in the treatment of sleep disordered breathing, Otol Clin N Am, 2003, pp. 473-493, vol. 36.
Van den Broek, E., et al., UPPP combined with radiofrequency thermotherapy of the tongue base for the treatment of obstructive sleep apnea syndrome, Eur Arch Otorhinolaryngol., Nov. 2008 Nov, pp. 1361-1365, vol. 265, No. 11.
Varghese, R., et al., Maxillomandibular advancement in the management of obstructive sleep apnea, International Journal of Otolaryngology, 2012.

(56) References Cited

OTHER PUBLICATIONS

Woodson, B.T., et al., A multi-institutional study of radiofrequency volumetric tissue reduction for OSAS, Otol H&N Surg., Oct. 2001, pp. 303-311, vol. 125, No. 4.

Woodson, B.T., et al., A randomized trial of temperature controlled radiofrequency, continuous positive airway pressure, and placebo for obstructive sleep apnea syndrome, Otol H&N Surg, 2003, pp. 848-861, vol. 128, No. 6.

\* cited by examiner

METHOD FOR TREATMENT OF SLEEP APNEA BY VENTRAL ONLY ABLATION OF THE TONGUE

CROSS REFERENCE TO RELATED APPLICATIONS

This application is a divisional of U.S. patent application No. 14/012,305, filed Aug. 28, 2013, now U.S. Pat. No. 9,554,852, which claims the benefit of and priority to U.S. Provisional Application No. 61/695,860, filed on Aug. 31, 2012, the entire contents of each of which are incorporated herein by this reference.

TECHNICAL FIELD

The present disclosure relates generally to medical apparatus and associated methods, and more particularly to electro-surgical devices such as RF ablation devices, affiliated tools, and methods for treating patients suffering from sleep apnea.

BACKGROUND

Sleep Apnea is a sleep disturbance (disorder) characterized by abnormal pauses in breathing or instances of abnormally low breathing, during sleep. An "apnea", or basically a pause in breathing can typically last from a few seconds to minutes, and may occur many times over a period of an hour. In one form of sleep apnea, commonly known as the Obstructive Sleep Apnea (OSA), a patient's normal breathing is interrupted by a physical block. As a result, not enough air reaches a patient's lungs, resulting in decreased airflow to the lungs, and consequently, snoring. Common symptoms of OSA include loud snoring, restless sleep, and consequently, fatigue and sleepiness during the daytime. Further, a patient suffering from obstructive sleep apnea can also suffer a stroke. Even further, patients suffering from sleep apnea can have memory loss due to reduced flow of oxygen to the brain caused by the decreased airflow to the lungs.

Conventionally, continuous positive airway pressure (CPAP) is one treatment for obstructive sleep apnea. CPAP treatments usually involve a patient wearing a mask or a similar device that fits over a patient's nose, or covering both the nose and the mouth of a patient. Usually, a tube connects the mask to a motor that blows air into the mask through the tube. The air pressure can be adjusted based on the needs and comfort level of the patient being treated. Generally it is the doctor's responsibility to decide what pressure setting is appropriate for the patient. There are many available masks with many variations. But, many patients have difficulty in tolerating forced air. Thus, claustrophobia and feelings of suffocation and/or panic attacks are also frequent complaints for patients who are treated using CPAP. Masks can also create sores, acne ulcers or annoying skin eruptions. Dry eyes from leaky masks can also be one annoying condition.

Other methods of treatment of sleep apnea include nasal valves, surgeries (e.g., to remove and tighten tissue around the airway to the lungs), and dental devices. Such surgeries can involve tongue repositioning, procedures concerning the patient's sinuses and valves, and various palatal techniques. However, surgeries can cause morbidity—pain and swallowing difficulties (i.e., patients have to be on soft diet for long periods of time). Patients who have undergone surgeries can also have difficulties in taste and speech. Also, conventional electrosurgical procedures cause deep thermal penetration because of the high temperatures (usually, 400 degrees Celsius to 600 degrees Celsius) used in the procedure. In many cases, even after performing surgeries, symptoms of sleep apnea can relapse after some time. Moreover, surgical procedures, if at all, can be performed on adults who are able to undergo surgical procedures.

In one traditional method of treating sleep apnea, RF ablation (RFA) devices are used to create lesions (typically four or more) at the base of the patient's tongue. Usually, such a method involves the doctor taking extra precaution so that the patient's lingual artery and hypoglossal and lingual nerves are avoided. The concept behind RFA involves dissociating soft tissue using bipolar radiofrequency energy. The devices comprise electrolytes in a conductive medium. A precisely focused plasma field (RF field) is created by exciting electrolytes in the conductive medium. As a result, energized particles or ions in the plasma field get sufficient energy to break organic molecular bonds within soft tissue at relatively low temperatures (usually, 40° C. to 70° C.).

Traditional methods involving RF ablation devices for treating sleep apnea can be painful and can also result in undesirable health complications of a patient. Examples of such complications include hematoma, dysphagia, dysarthria, deformity, aspiration, and other undesirable complications. Consequently, patients treated using traditional RF ablation methods have to be hospitalized and intubated, thereby increasing medical costs and exposing patients to health risks.

Therefore, there is a long-felt but unresolved need for an improved medical device and associated tools and methods or procedures that treat sleep apnea without causing swelling or hematoma of a patient's tongue. Further, the improved procedure should cause significantly less pain to a patient, should preferably not involve intubation or hospitalization of any kind. Even further, the procedure should result in reduced morbidity arising from changes in swallowing. Also, the procedure should minimize the risk of relapse of the symptoms of sleep apnea.

BRIEF SUMMARY OF THE DISCLOSURE

Briefly described, and according to one embodiment, aspects of the present disclosure generally relate to RF ablation procedures, affiliated devices and tools to treat sleep apnea in patients. In one embodiment, the ablation is generally performed on the ventral surface of a patient's tongue. Accordingly, the procedure as described herein is termed as Ventral Only Ablation of Tongue (VOAT), and is generally an office-based procedure without requiring hospitalization or intubation for patients. In one aspect, the disclosed procedure is more effective than other tongue ablation techniques to move the posterior tongue base away from the posterior pharyngeal wall in patients suffering from sleep apnea, thereby creating more airway passage for allowing airflow to the lungs. In another aspect, the disclosed procedure is performed in a superior plane along a longitudinal (i.e., anterior to posterior) axis of the patient's tongue. According to aspects as described herein, it will be better understood from the following discussions that contraction resulting from the scarring induced by the procedure causes the posterior tongue base to move away from the posterior pharyngeal wall in patients suffering from sleep apnea.

These and other aspects, features, and benefits of the claimed invention(s) will become apparent from the following detailed written description of the preferred embodiments and aspects taken in conjunction with the following drawings and Exhibits, although variations and modifications thereto may be effected without departing from the spirit and scope of the novel concepts of the disclosure.

BRIEF DESCRIPTION OF DRAWINGS

The accompanying drawings illustrate one or more aspects of the disclosure and, together with the written description, serve to explain the principles of the disclosure. Wherever possible, the same reference numbers are used throughout the tables and exhibits.

DETAILED DESCRIPTION

For the purpose of promoting an understanding of the principles of the present disclosure, reference will now be made to the embodiments illustrated in the attached Exhibits and drawings, and specific language will be used to describe the same. It will, nevertheless, be understood that no limitation of the scope of the disclosure is thereby intended and any alterations and further modifications of the described or illustrated embodiments and any further applications of the principles of the disclosure as illustrated therein are contemplated as would normally occur to one skilled in the art to which the disclosure relates. All limitations of scope should be determined in accordance with and as expressed in the claims.

Aspects of the present disclosure generally relate to RF ablation procedures, affiliated devices and tools to treat sleep apnea in patients. In one embodiment, the ablation is generally performed by insertion of an RF electro-surgical ablation device or needle into the ventral surface of a patient's tongue.

There are various benefits of the Ventral Only Ablation of the Tongue (VOAT) procedure described herein. Examples of such benefits include, but are not limited to, quick recovery time, minimal risk to a patient's health, minimal incision, less sensitive incision, and no hospitalization or intubations. In particular, the VOAT procedure can be performed in an office setting with reduced surgical support equipment and personnel.

Figure 1:
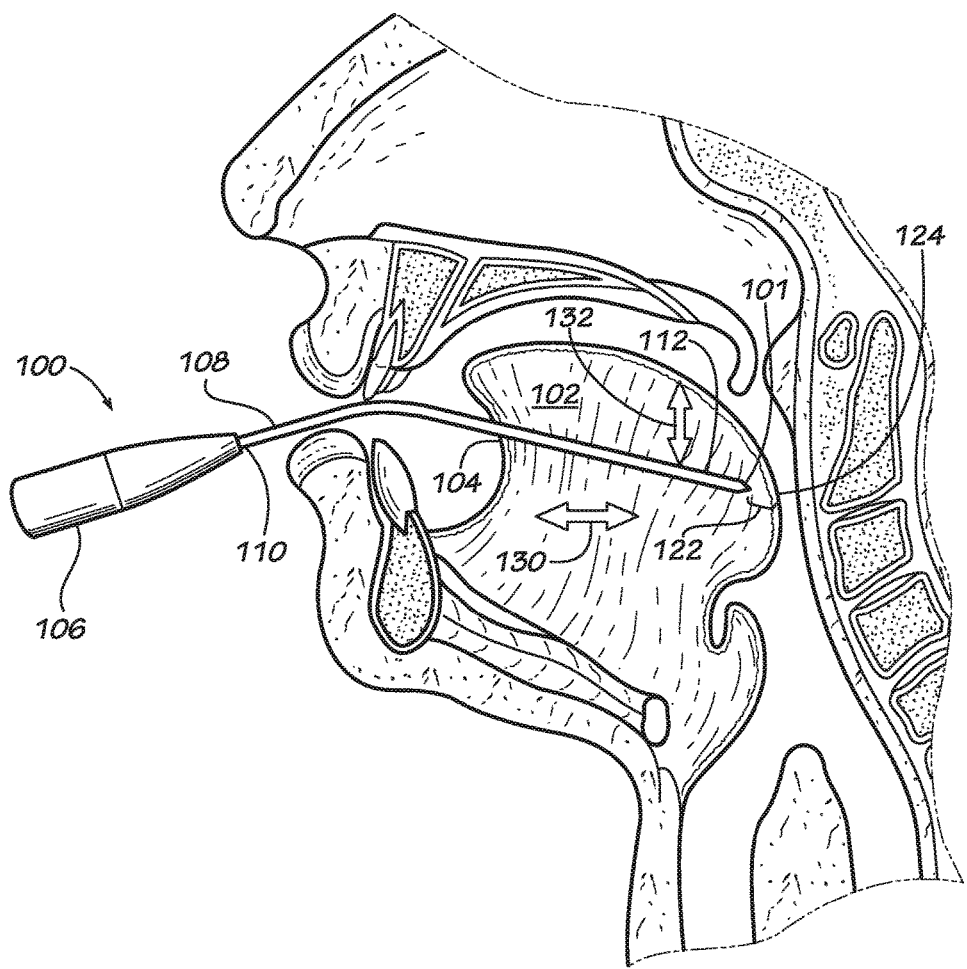
FIG. 1 is a schematic cross sectional view of a patient undergoing treatment according to aspects of the invention wherein the electro-surgical instrument is shown inserted into the tongue via an insertion point on the ventral surface of the tongue.

FIG. 1 is a schematic cross sectional view of a patient undergoing treatment. As shown in FIG. 1, an elongate, needle-like electro-surgical device 100 having a sharp tip 101 is inserted into the tongue 102 at an insertion point 104 on the ventral surface of the tongue. As shown in FIG. 1, electro-surgical device 100 comprises a handle 106 and an elongate member 108 extending from the handle wherein the elongate member has a proximal end 110 and a distal end 112 forming an insertion tip 101. As shown in FIG. 1, when the electro-surgical device 100 is fully inserted in the patient's tongue, distal end 112 is spaced a distance 122 from a terminal point 124 on the dorsal surface at the base of the tongue.

As an alternative methodology for determining an appropriate insertion depth for the procedure, considered in classic geometrical terms, FIG. 1 also shows arrows 130, 132, which represent a distance of insertion of the electro-surgical device 100 into the tongue in an X-Y coordinate system, to as to provide a different frame of reference for insertion of the probe or tip. The lateral distance indicated by arrow 130 represents a desired insertion ventral insertion depth, anterior to posterior, relative to a premeasured lateral (X-axis) depth of the patient's tongue, while the vertical distance indicated by arrow 132 represented a desired insertion depth, superior to inferior plane, relative to a premeasured vertical (Y-axis) depth of the patient's tongue, measured from the dorsal surface of the tongue, which as seen in the figure bears a curvature or radius.

FIG. 1 thus shows the vertical or near-vertical (i.e., superior to inferior) plane 132 utilized in conventional RF ablation (RFA) procedures. Forming lesions in the tongue oriented in the superior to inferior plane 132 can cause more scarring. As described herein, in accordance with aspects of the invention, lesions are formed predominantly in the interior of the tongue in an anterior to posterior plane 130. Less scarring results from forming lesions oriented in the anterior to posterior plane 130. Consequently VOAT procedures are more apt to move the posterior tongue base away from the posterior pharyngeal wall.

Figure 2:
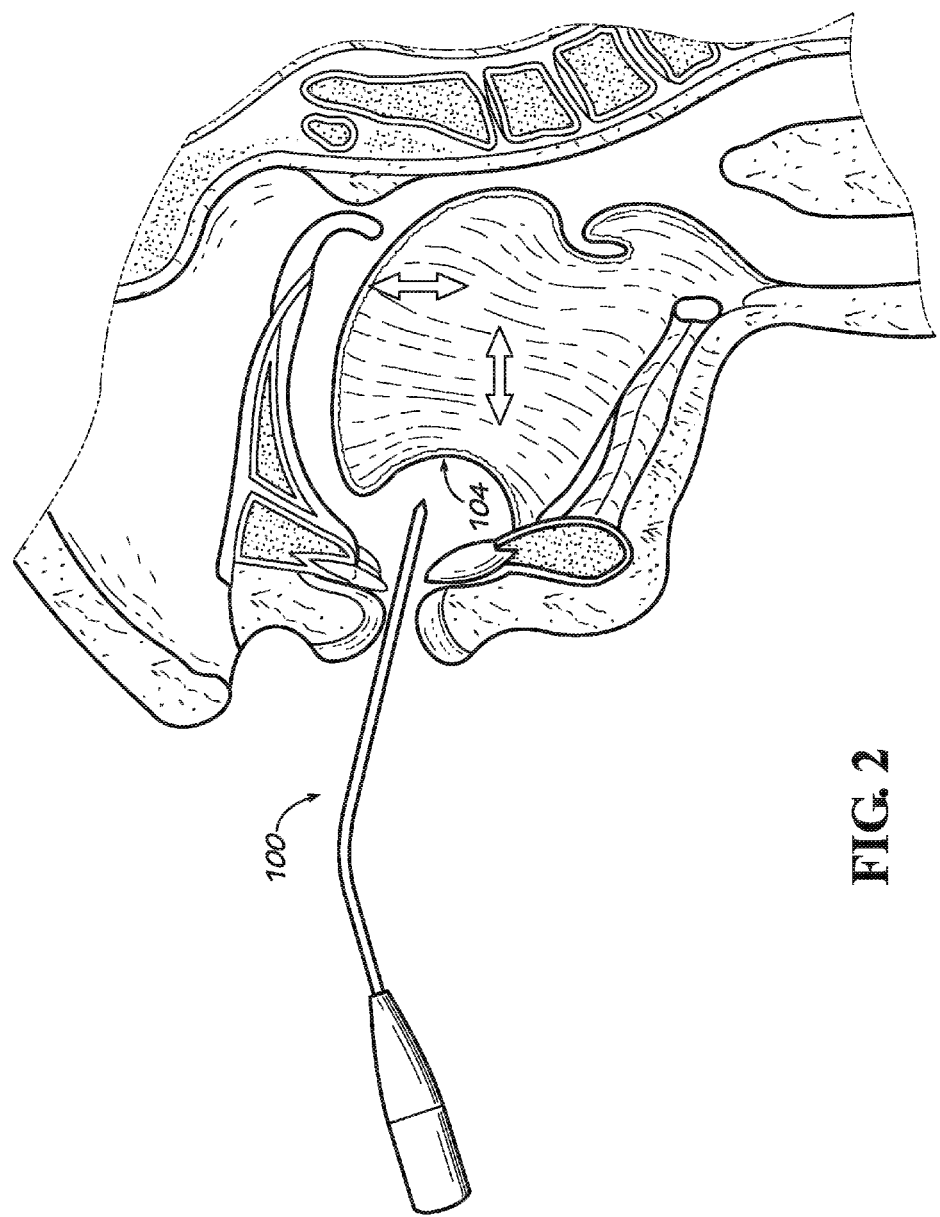
FIG. 2 is a schematic cross sectional view of a patient undergoing treatment according to aspects of the invention wherein the electro-surgical instrument is shown positioned for insertion into the ventral surface of the tongue.

FIG. 2 is a schematic cross sectional view of a patient undergoing treatment according to aspects of the invention wherein electro-surgical device 100 is shown positioned for insertion into the ventral surface of the tongue at an insertion point 104.

Figure 3:
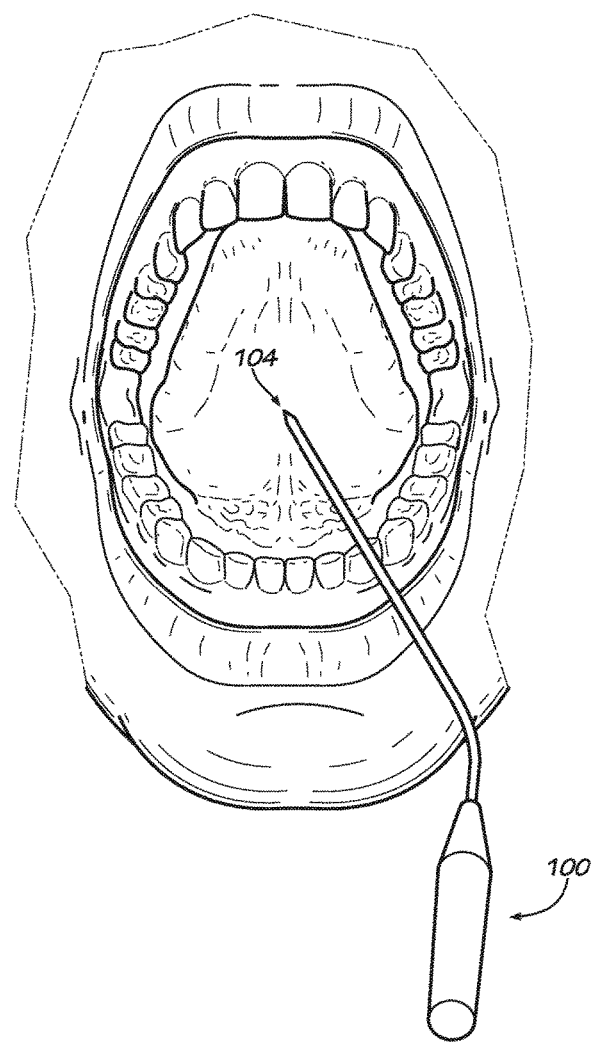
FIG. 3 is a front view of a patient undergoing treatment according to aspects of the invention wherein the electro-surgical instrument is shown positioned for insertion into the ventral surface of the tongue.

FIG. 3 is a schematic front view of a patient undergoing treatment according to aspects of the invention wherein the electro-surgical device 100 is shown positioned for insertion into the ventral surface of the tongue at the insertion point 104.

Figure 4A:
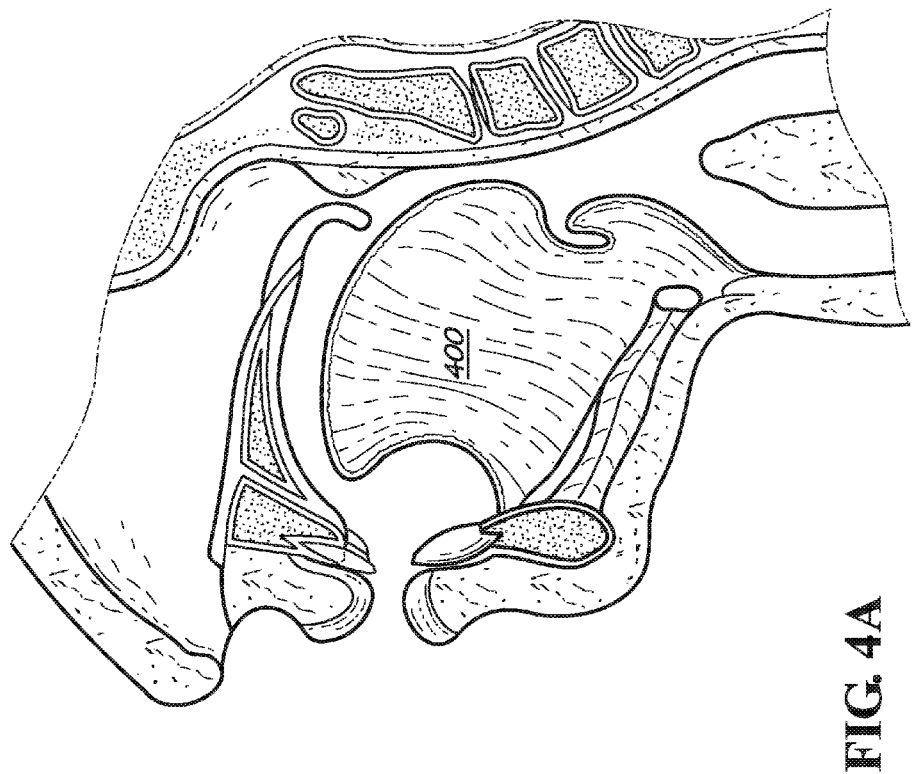
FIG. 4A is a schematic cross sectional view of a patient prior to the procedure.

FIGS. 4A-4G illustrate a method according to aspects of the invention wherein a retractor device is used in conjunction with the electro-surgical instrument, to assist in guiding the insertion of the electro-surgical instrument or probe 100 and determine an appropriate insertion depth. In this regard, FIG. 4A is a schematic cross sectional view of a patient prior to the procedure showing the patient's tongue 400.

Figure 4B:
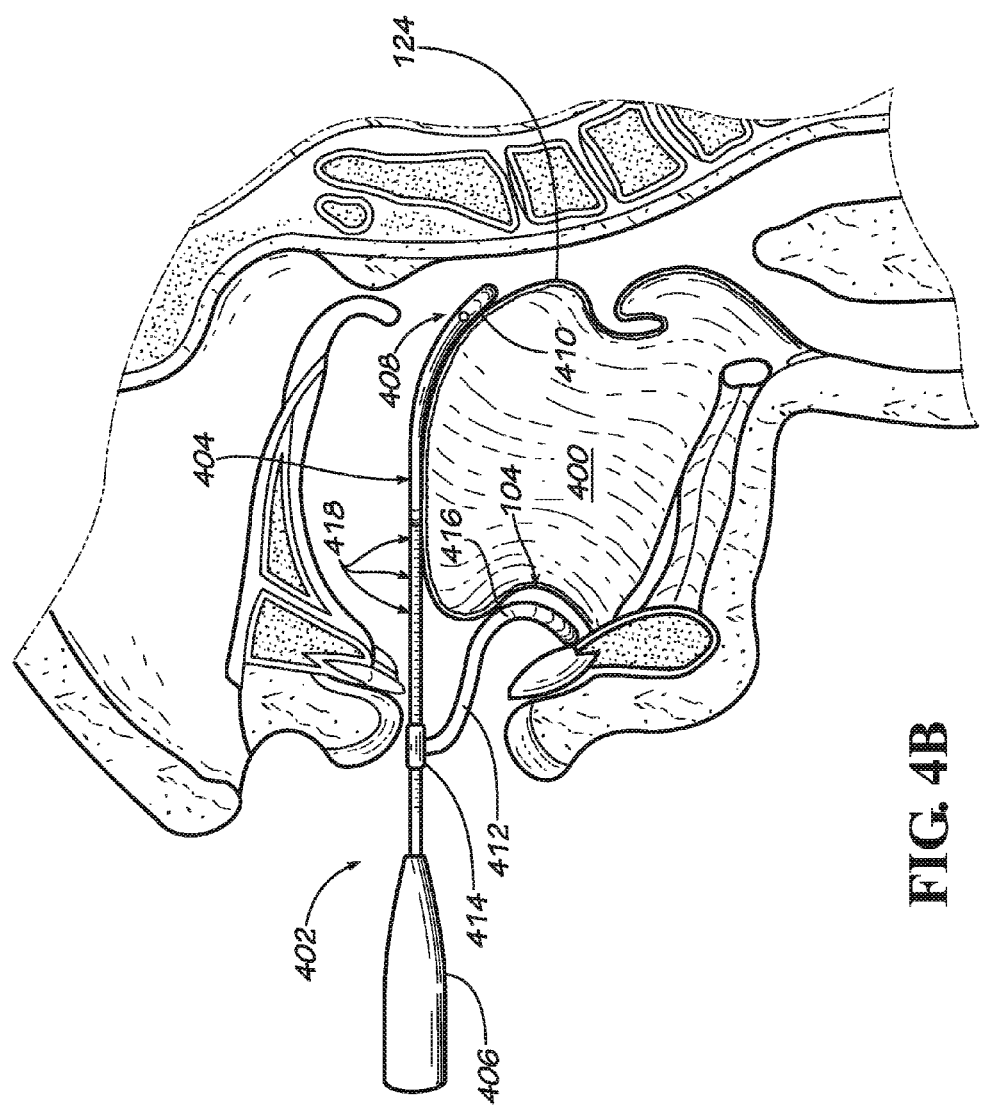
FIG. 4B is a schematic cross sectional view of a patient showing placement of a retractor device on the tongue of the patent according to aspects of the invention before the tongue engaging portion of the retractor device has been slid forward to contact the ventral surface of the tongue.

FIG. 4B is a schematic cross sectional view of the patient showing placement of a retractor device 402 on the tongue 400. The retractor device 402 is used to lift the tongue to expose the ventral surface of the tongue and desired insertion point, maintain the tongue in a lifted position to avoid interference or contact with the electro-surgical device 100 during its use, contact with the dorsal surface 124 of the tongue, and provide a way or means to measure the patient's tongue for purposes of determining an appropriate insertion depth for the RF probe.

As shown in FIG. 4B, device 402 includes an elongate member 404 extending from a handle 406 having a distal end 408, a flattened region 410 at the distal end 408 which is bent downward for contacting a dorsal surface at the base of the tongue and a loop-like retractor portion 412 extending downwardly from a clamp 414. As shown in FIG. 4B, clamp 414 is adapted to slide along the length of elongate member 404. Retractor portion 412 comprises a loop-like tongue-engaging portion 416 which is adapted to contact the ventral surface of the tongue near the insertion point when clamp 414 is slid forward toward flattened region 410.

As also shown in FIG. 4B, measuring indicia 418 are shown along the length of the elongate member 404.

Figure 4C:
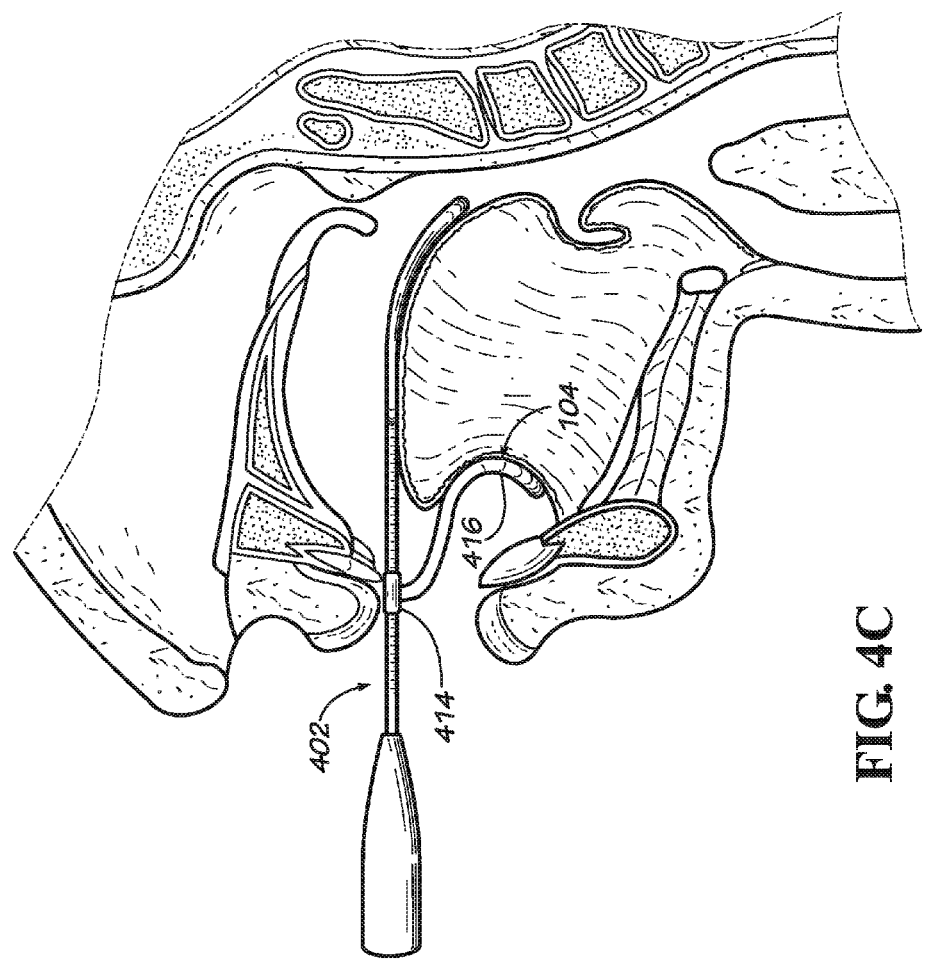
FIG. 4C is a schematic cross sectional view of a patient showing the placement of a retractor device on the tongue of the patent according to aspects of the invention after the tongue engaging portion of the retractor device has been slid forward to contact the ventral surface of the tongue.

FIG. 4C is a schematic cross sectional view of a patient showing the placement of a retractor device 402 on the tongue of the patient. As shown in FIG. 4C, the clamp 414 of device 402 has been slid forward such that tongue engaging portion 416 contacts the ventral surface of the tongue. Preferably, the insertion point 104 is exposed within the area defined by the loop of the tongue-engaging portion 416.

Figure 4D:
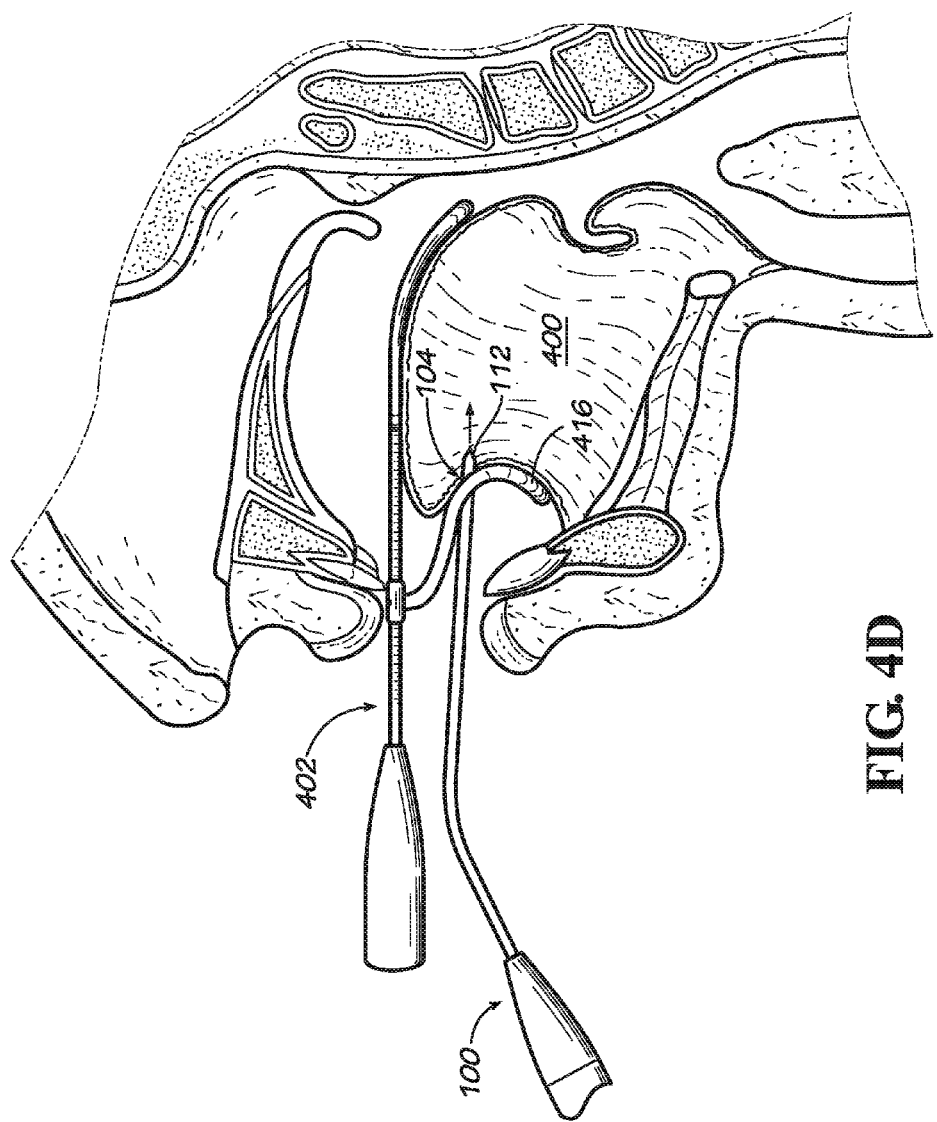
FIG. 4D is a schematic cross sectional view of a patient showing the placement of a retractor device on the tongue of the patient showing the tip of the electro-surgical device being inserted into the ventral surface of the tongue through an opening in the tongue engaging portion of the retractor.

FIG. 4D is a schematic cross sectional view of a patient showing placement of retractor device 402 on the tongue 400 of the patient and showing the distal end 112 of electro-surgical device 100 being inserted into the ventral surface of the tongue through an opening or insertion point 104 in the tongue-engaging portion 416 of the retractor device 402.

Figure 4E:
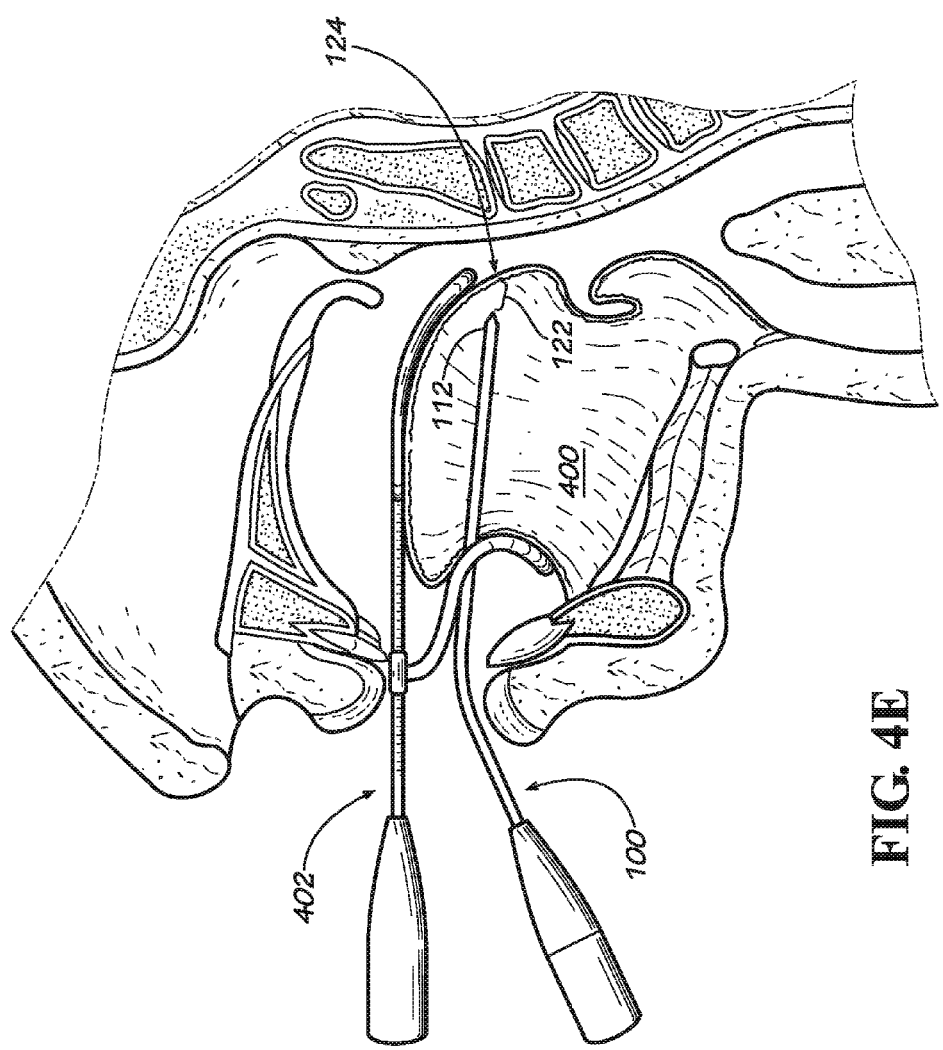
FIG. 4E is a schematic cross sectional view of a patient showing the electro-surgical device fully inserted into the tongue and showing the tip of the device located at a predetermined distance from the terminal point on the dorsal surface of the base of the tongue.

FIG. 4E is a schematic cross sectional view of a patient showing electro-surgical device fully 100 inserted into the tongue and showing the distal end 112 of electro-surgical device 100 spaced at a distance 122 from the terminal point 124 on the dorsal surface of the base of the tongue. According to some embodiments, distance 122 is 5-8 cm.

Figure 4F:
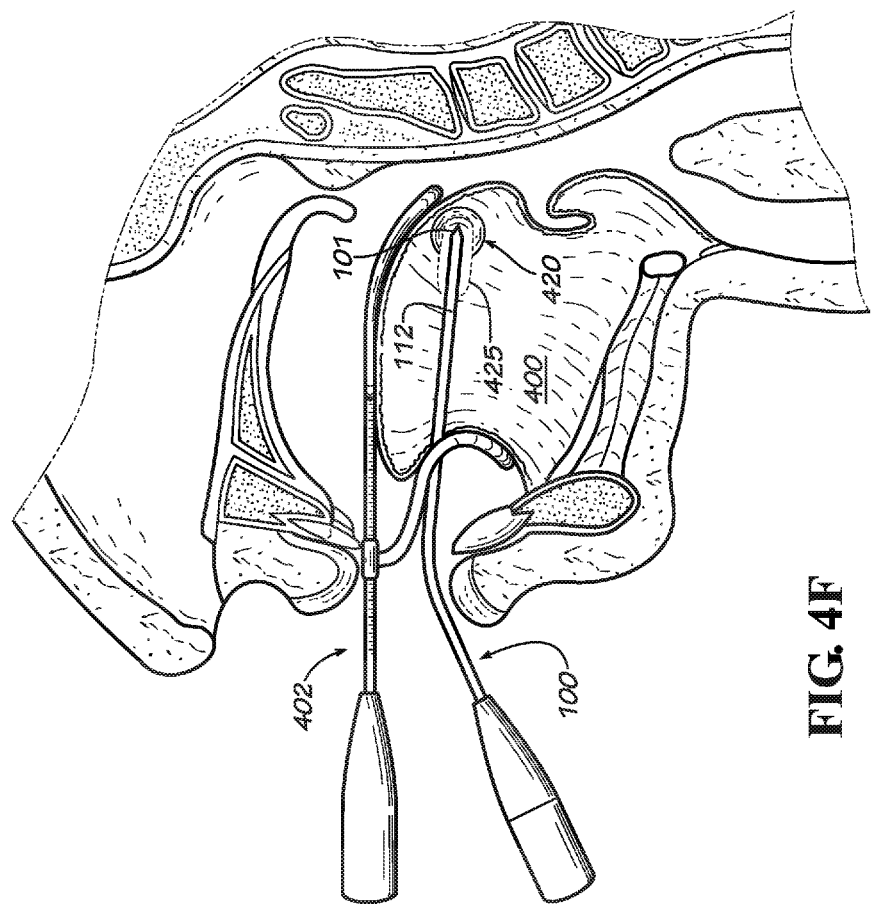
FIG. 4F is a schematic cross sectional view of a patient showing the electro-surgical device fully inserted into the tongue and showing the tip of the device located at a distance from the terminal point on the dorsal surface of the base of the tongue wherein energy is being applied to tissue adjacent the tip of the probe.

FIG. 4F is a schematic cross sectional view of a patient showing electro-surgical device 100 fully inserted into the tongue 400 wherein radio frequency (RF) energy 420 is being applied to tissue adjacent the tip 101 at the distal end 112 of the electro-surgical device 100. Application of RF energy at the appropriate energy level results in formation of a lesion 425 within the cavity or void formed by insertion of the needle-like electro-surgical device.

Figure 4G:
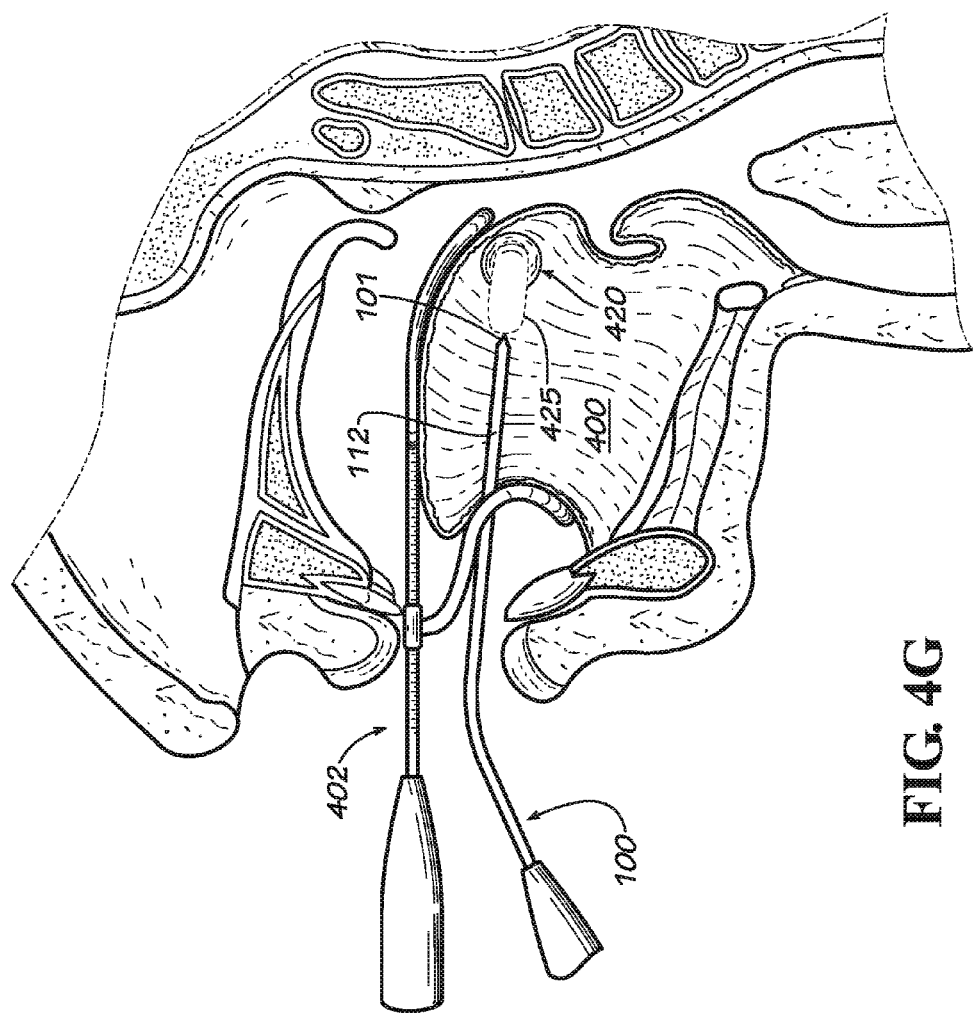
FIG. 4G is a schematic cross sectional view of a patient showing the electro-surgical device inserted into the tongue but withdrawn a predetermined distance from the terminal point, and showing the tip of the device located at a distance withdrawn from the terminal point on the dorsal surface of the base of the tongue wherein energy is being applied to tissue adjacent the tip of the probe.

According to aspects of the invention, the lesion 425 may be elongated by gradual withdrawal of the electro-surgical device 100, while applying RF energy, so as to form an elongate, axial lesion. FIG. 4G is a schematic cross sectional view of a patient showing electro-surgical device 100 partially withdrawn (retracted) from the maximum extent of insertion in the tongue 400 as in FIG. 4F, wherein radio frequency (RF) energy 420 is applied to tissue adjacent the tip 101 at the distal end 112 of the electro-surgical device 100 after an initial application of energy, with a subsequent application of energy to elongate the lesion 425. Application of RF energy at the appropriate energy level results in formation of an elongated lesion 425 within the cavity or void formed by insertion of the needle-like electro-surgical device 100. The elongated extent of the lesion 425 may be controlled by the power settings of the electro-surgical device, as well as the amount of withdrawal from the maximum extent, and also the application of discrete instances of energization followed by withdrawal a predetermined extent, in stages or steps.

Figure 5:
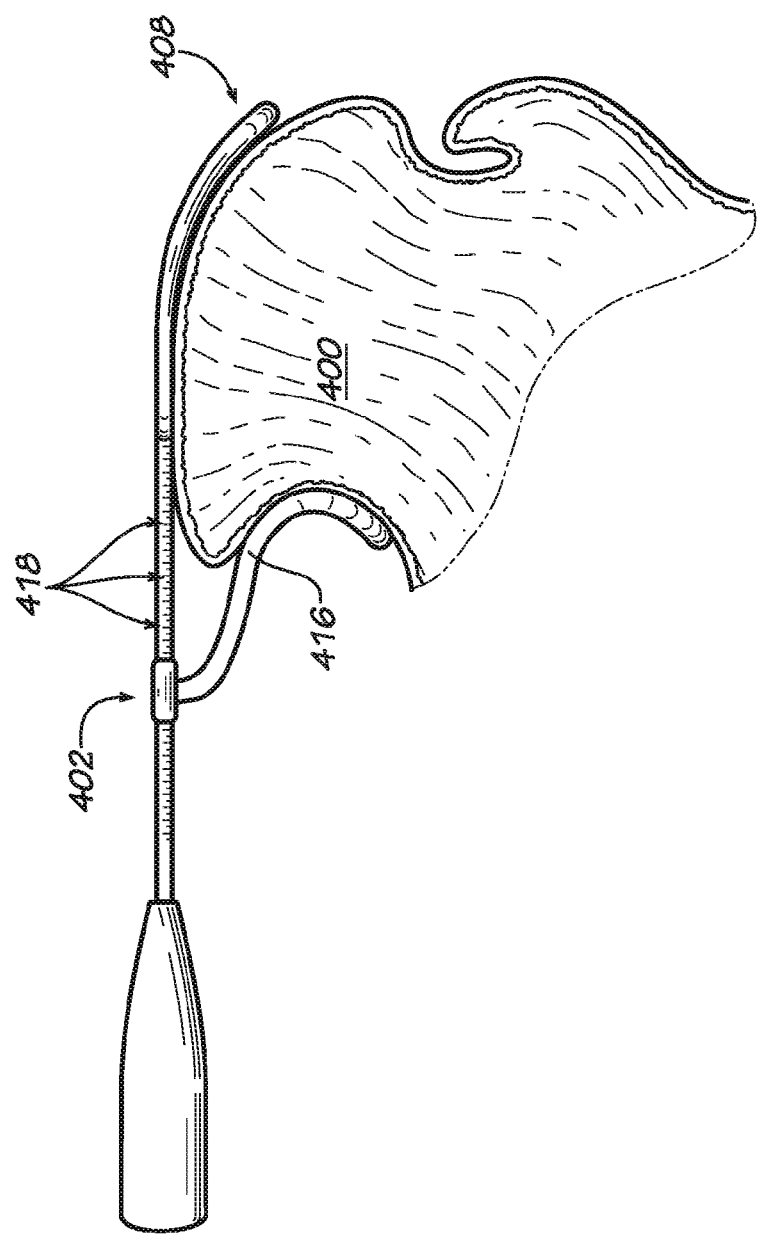
FIG. 5 is a side view showing placement of a retractor device on the tongue of the patient wherein measuring indicia are shown on the device and wherein the retractor portion of the device is slid forward to contact the ventral surface of the tongue.

FIG. 5 is a side view showing placement of retractor device 402 on the tongue 400 of the patient, wherein measuring indicia or markings are shown on the device and wherein the retractor portion 416 of the device is slid forward to contact the ventral surface of the tongue. The distal portion 408 of the retractor device 402 contacts with the dorsal surface of the tongue 400.

Figure 6:
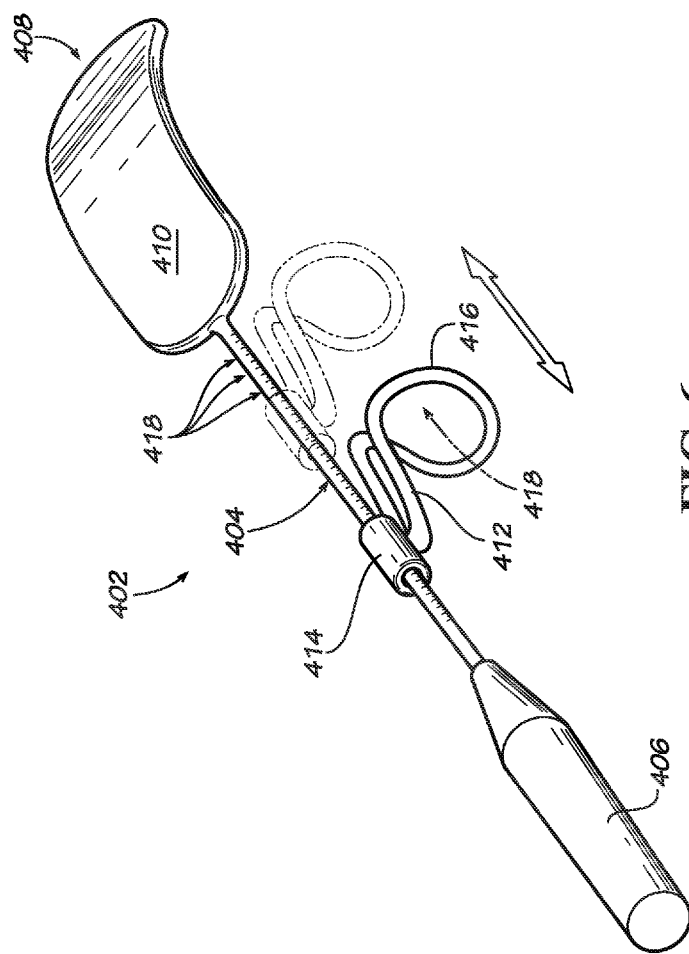
FIG. 6 is a schematic perspective view of a retractor device comprising an elongate member having proximal and distal ends, a flattened region at the proximal end which is bent downward for contacting a dorsal surface at the base of the tongue, a handle adjacent the distal end, and a retractor extending from a clamp adapted to slide along the length of the elongate member wherein measuring indicia are shown along the length of the elongate member and illustrating how the retractor portion of the device can be slid back and forth along the length of the device.

FIG. 6 is a schematic perspective view of a retractor device 402. As shown in FIG. 6, device 402 comprises an elongate member 404 having a proximal end adjacent a handle 406 and a distal end 408, a flattened region 410 at the distal end 408 which is bent downward for contacting a dorsal surface at the base of the tongue, a handle 406 adjacent the proximal end, and a loop-like retractor 412 extending from a clamp 414 adapted to slide along the length of the elongate member 404. Retractor 412 includes a tongue engaging portion 416 which is depicted as an open loop in FIG. 6. The space 418 defined by the loop 416 provides a guide for insertion of the electro-surgical instrument (not shown in this figure). The space 418 may be made smaller, as desired, or may include a separate insertion guide (not shown) positioned within the space so as to facilitate and guide insertion of the electro-surgical instrument.

As also shown in FIG. 6, device 402 includes measuring indicia 418 along the length of elongate member 404. As shown in FIG. 6, clamp 414 and retractor portion 412 can be slid back and forth along the elongate member 404 of device 402. In use, device 402 is placed on the tongue such that flattened region 410 is in contact with a dorsal surface at the base of the tongue with clamp 414 slid backward toward handle 406. Clamp 414 and attached retractor portion 412 is then slid forward toward the distal end 408 of device 402 until tongue engaging portion 410 contacts the dorsal surface of the tongue. Once positioned and engaged on the tongue, device 402 can be used to manipulate and position the tongue into the proper position for the electro-surgical procedure. The electro-surgical instrument can be inserted through the open loop of the tongue engaging portion 416 of retractor portion 412.

Figure 7:
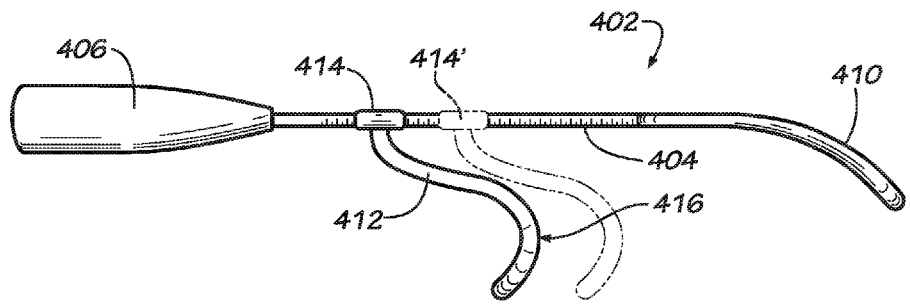
FIG. 7 is a schematic side view of the retractor device of FIG. 6.
Figure 8:
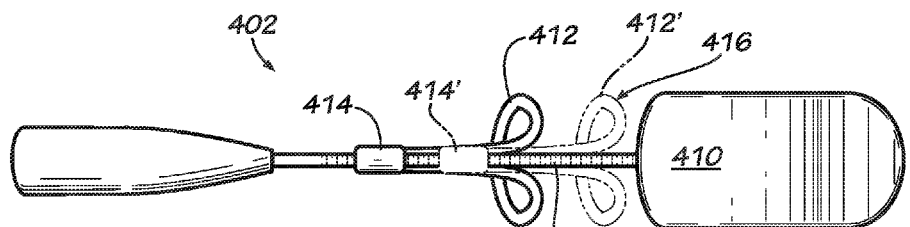
FIG. 8 is a schematic top view of the retractor device of FIG. 6.

FIG. 7 is a schematic side view of the retractor device 402 of FIG. 6. FIG. 8 is a schematic top view of the retractor device 402 of FIG. 6. As shown in FIGS. 7 and 8, clamp 414 and retractor portion 412 can be slid back and forth along the elongate member 404 of the device. In accordance with one aspect, the clamp 414 can be moved to a different position 414', thereby adjusting the position of the retractor portion 412 to that shown at 412'. A holding means such as a set screw, rachet and cog, compression clamp, elastic constrictor, or similar device may be used to hold the clamp 414 in position after adjusting to the patient's tongue.

Figure 9:
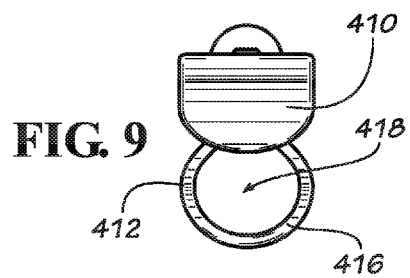
FIG. 9 is a schematic back view of the retractor device of FIG. 6.

FIG. 9 is a schematic back view of the retractor device of FIG. 6 showing the open loop and space 418 formed by the retractor portion 412 and tongue engaging portion 416.

Figure 10:
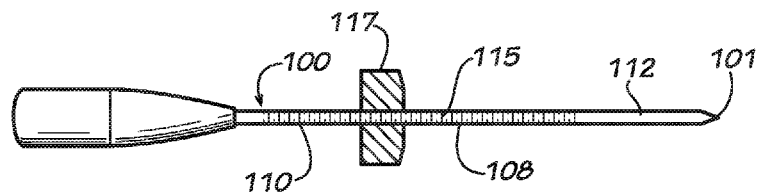
FIG. 10 is a schematic of an electro-surgical device comprising an elongate member having measuring indicia along the length of the elongate member and an adjustable stop adapted to engage the ventral surface of the tongue or the tongue engaging portion of the retractor of a retractor device thereby limiting the insertion depth of the tip of the electrosurgical device into the tongue of a patient.

FIG. 10 is a schematic of an electro-surgical device 100 comprising an elongate member 108 having measuring indicia 115 along the length of the elongate member 108 and an adjustable stop 117 adapted to slide along the length of elongate member 108. Adjustable stop 117 can also comprise a securing means (not show) such as set screw, ratchet, compression clamp, elastic constrictor, etc. which allows the adjustable stop to be secured to elongate member 108 at a desired position. Adjustable stop 117 can be used to limit the insertion depth of the tip 101 of electro-surgical device 100. In use, adjustable stop 117 can be set and secured at a position to achieve the desired insertion depth into the tongue. According to one aspect, the insertion depth is the distance between the front surface of adjustable stop 117 and the tip 101 of electro-surgical device 100. As device 100 is inserted into the tongue, adjustable stop 117 will contact the ventral surface of the tongue thereby limiting the insertion depth of the tip of the electrosurgical device into the tongue of a patient. Alternatively, the adjustable stop 117 may contact the loop-like retractor portion 412 or guide of the retractor device 402 (see FIG. 4F, with stop not show), to prevent further insertion.

An electro-surgical device 100 comprising an adjustable stop 117 as shown in FIG. 10 can also be used with a retractor device such as the device shown in FIGS. 6-9. When used with such a device, adjustable stop 117 of electro-surgical device 1000 can be adapted to contact tongue engaging portion 416 of retractor portion 412 when the electro-surgical device is inserted to the desired insertion depth.

The electro-surgical device 100 is preferably an RF ablation device. The device can comprise a bipolar element on a 1-2 mm wide shaft, the shaft emitting a focused RF field (beam) for performing the VOAT procedure. In one exemplary embodiment, such a wand is the Coblation™ Reflex 45 manufactured by Arthrocare Corporation, in Austin, Tex. According to another exemplary embodiment, a Celon Lab ENT wand and RF generator manufactured by Olympus Medical Systems India, Olympus Corporation (Japan) can be employed.

As described above, the electro-surgical device 100 is guided into position to a predetermined distance 122 (FIG. 1) from the dorsal surface of the tongue by measurement or by feel prior to puncture of the dorsal surface. Although puncture is preferable to avoid, it is not believed that puncture is a significant contraindication of the procedure, and that the lesion formed from withdrawal may still be effective.

According to another aspect, the tip 101 of the electro-surgical device 100 can be guided into an appropriate position using other techniques such as RF image guidance such as a Fusion ENT Navigation System manufactured by Medtronic, Inc., Minneapolis, Minn.

Exemplary details of steps involved in a VOAT procedure on a patient suffering from sleep apnea are described in the discussions that follow.

According to an aspect, a VOAT procedure requires a patient to be moderately sedated. Moderate sedation is induced with the assistance of a nurse anesthetist or anesthesiologist. After sedation, the ventral aspect of the patient's tongue is exposed by retracting the patient's lower lip and jaw inferiorly, and the tongue posteriorly. Usually, sufficient tension is needed to spread out the mucosa over the under surface of the tongue and submandibular gland duct openings.

According to aspects as described herein, the wand or probe of the electro-surgical instrument 100 is positioned near the base of the tongue for puncturing the mucosa about 5-10 mm superior to the submandibular gland duct openings in the midline. After the mucosa is punctured by insertion of the tip 101 of the wand, the wand is slowly advanced in the midline sagittal plane along the midline fusion plane of the tongue. The wand is typically set at a power level of 6 (in the preferred Coblation™ Reflex 45) for 10 seconds, and held over a distance of 5-8 cm from the base of the tongue. Advancing along the midline avoids contact of the probe and radio waves in any significant fashion with the arteries and veins of the tongue. Further, it also avoids the lingual and hypoglossal nerves.

The scarring or lesion created in the manner as described in the above procedure has its longest axis in the anterior and posterior dimension of the tongue, as opposed to the more vertically oriented lesions (See FIG. 1). It will be understood and appreciated that the contraction of the scar (caused due to the radiofrequency induced scarring) reduces the physical blockage to the airway passage, thereby opening up the airway passage to the patient's lungs. Therefore, scarring according to VOAT procedure described herein is less than in previously described vertical planes (e.g., see FIG. 1). Also, there is no significant bleeding, according to this procedure.

In the discussions that follow, patient data as a result of performing VOAT procedure are discussed.

Patient data as a result of performing VOAT procedure on three different patients is described below. The three de-identified patents are referred to by the initials "RJ", "MT", and "EG". Before describing further details of these patients, metrics used in determining the severity of sleep apnea is described. One index used in measuring sleep apnea is AHI.

Specifically, AHI is an index used to assess the severity of sleep apnea based on the total number of complete cessations (apnea) and partial obstructions (hypopnea) of breathing occurring per hour of sleep. The pauses (that last for 10 seconds or more) in breathing are associated with a decrease in oxygenation of the blood. In general, the AHI can be used to classify the severity of sleep apnea (mild 5-15, moderate 15-30, and severe greater than 30).

The patient RJ is a 65 year old asthma patient having gastroesophageal reflux disease (GERD) OSA, and with CPAP intolerance. The patient experienced nightly headaches. The patient had a surgery, i.e., bilateral maxillary balloon sinuplasty. However, OSA continued past her surgery. VOAT procedures were performed on her twice over a three month period. Prior to performing the VOAT, AHI levels were 15 events/hour. Post-VOAT levels were 1.1 events/hour. As a result, a 93% improvement in AHI levels, as a consequence of the VOAT procedure was recorded. CPAP treatments were discontinued for this patient.

Patient MT had an initial AHI of 105. After CPAP, conditions were worse and patient did not want tracheostomy. Patient had previously undergone tongue resection palate and hyoid suspension procedures. The patient's AHI of 87.9 was still uncontrolled with CPAP. After five in-office VOAT procedures, the AHI levels for this patient dropped to 41 and were 100% controlled with Bi-level Positive Airway Procedure (BIPAP). VOAT supplemented with a Bi-level Positive Airway Procedure (BIPAP) was therefore able to control the sleep apnea of this patient by 100%.

Patient EG was CPAP intolerant and had a pre-VOAT AHI level of 29.9. However, post-VOAT AHI was measured as 0.9 for this patient.

Overall results of performing VOAT procedures on several patients were evaluated. Only one (1) out of 300 patients who had VOAT procedures was exposed to morbidity. Also, only one (1) patient out of 300 patients had a small anesthetic area tongue. Only two (2) patients out of 300 who had VOAT procedures were exposed to minor bleeding.

Figure 11:
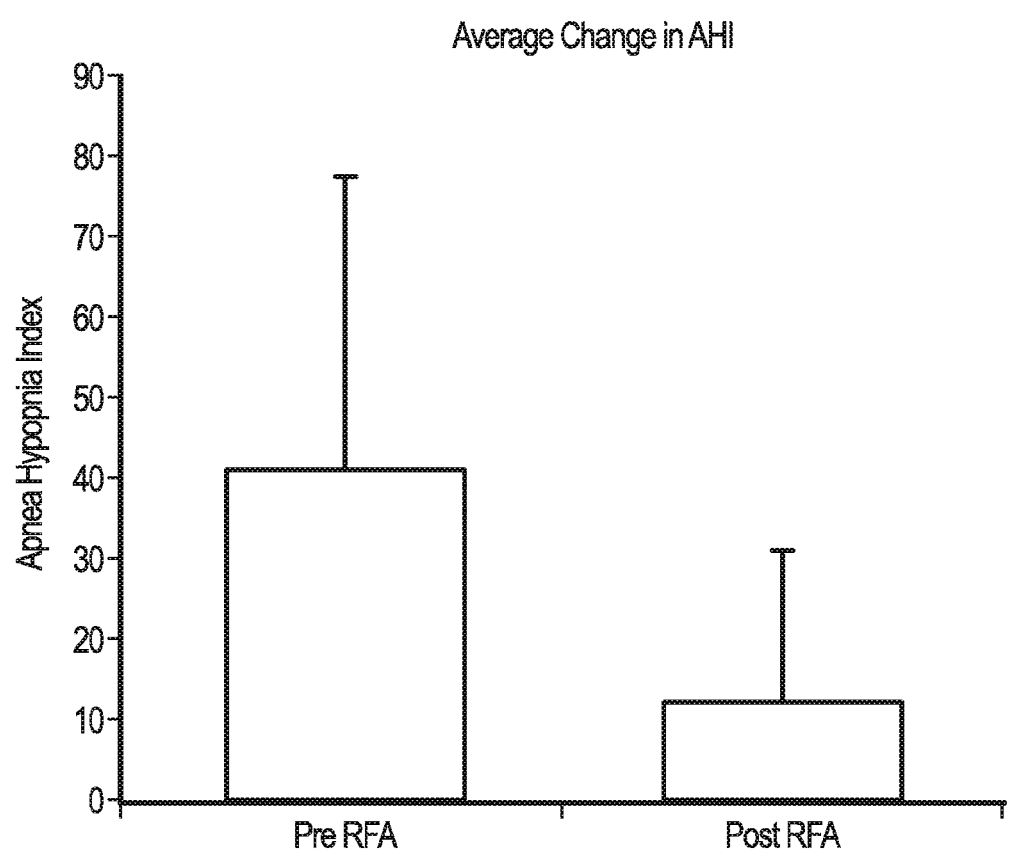
FIG. 11 is a bar chart showing overall results of performing VOAT procedures on several patients.

FIG. 11 is a bar chart showing overall results of performing VOAT procedures on several patients. As shown in FIG. 11, average changes in AHI, pre-VOAT and post-VOAT, are indicated. In what follows, exemplary affiliated tools used in VOAT procedures (e.g., along with the RF ablation device) are described.

Experimental Data

The practice of this invention can be further understood by reference to the following examples, which are provided by way of illustration only are not intended to be limiting.

Study Design:

Retrospective consecutive case series of 15 patients treated with ventral only ablation of the tongue (VOAT) with comparison of pre and post-operative polysomnography (PSG) results are discussed.

Setting: Private practice otolaryngology clinic.

Subjects and Methods:

98 consecutive patients' records were reviewed. Patients who were referred for intolerance of continuous positive airway pressure therapy (CPAP) therapy, and who were subsequently treated with radiofrequency ablation of the tongue base were included and records reviewed. Patients who did not have their post-operative polysomnography (PSG) data were excluded as were any patients with concurrent interventions. Fifteen (15) patients were identified with these criteria and their AHI, and pre and post operatively were compared.

Results: The average pre-operative AHI of 34.2, post-operative average AHI of 9.98 were significantly different with a p of 0.002. The average improvement in AHI was 24.34 or (72.3% improvement). Three patients (20%) failed to improve significantly. Overall complication rate 300 procedures reviewed showed three patients who required observation for minor bleeding and one patient with long term tongue tip numbness.

Conclusion: VOAT modification of the radiofrequency submucosal ablation of the tongue is a viable alternative to the current technique with minimal morbidity.

According to an aspect, VOAT is a less-invasive variation of the radiofrequency ablation of the base of tongue procedure (RFA BOT). An adjunctive treatment alternative for mild to moderate or severe OSA is therefore proposed.

Introduction: CPAP remains the gold standard for OSA, but 29-83% of patients are CPAP intolerant or non-compliant [1, 2]. Surgical therapy for obstructive sleep apnea has been attempted with a variety of procedures. Nasal procedures are a prerequisite to success if nasal obstruction is present. The pharyngeal level obstructions are more problematic. Tonsillectomy and adenoidectomy are appropriate for a minority of adult OSA patients. Uvulopalatopharyngoplasty (UPPP) is a significantly morbid operation and, although commonly performed, is only effective for a minority of the OSA population. UPPP only has a success rate of 49% after 7 years with 30% of patients reporting swallowing difficulties [3]. Hyoid suspensions require a 2-5 day hospital stay and carry post op complaints regarding taste, speech, swallowing, and pain [4]. Nasal procedures are appropriate as needed to improve nasal function and open the airway. They are commonly performed but have not been able to show a significant impact on adult OSA3. Maxillofacial surgery is as effective as CPAP but has a significant post op course requiring 6 weeks of soft diet [5].

Within the last decade, there has been an increasing use of RFA BOT to help alleviate the need for more invasive surgery as part of a multilevel pharyngeal treatment for sleep apnea. The technique, as it is generally described, involves placing a series of 4-5 lesions across the tongue base in a more or less superior inferior plane. The technique relies upon tissue heating, death, scarring and eventual contracture to achieve volume reduction at the tongue base.

RFA BOT results are reported to yield a 31% reduction in short term (<12 month) and 45% reduction in long-term (>24 month) for respiratory disturbance index (RDI) levels [6]. Controlled study of treatment schemes for RFA suggests additional improvement in outcomes with repeated treatments [7].

The current RFA BOT method has some drawbacks which include possible bleeding from branches of the lingual vascular complex midline which can cause swelling and potential airway problems. The vascular structures at this level cannot be identified readily from surface landmarks at this level.

Additionally, the lesions' long axis of contracture and thus volume reduction is in a superior and inferior orientation. This theoretically results in less opening of the pharynx than if the lesions were anterior to posterior orientation. Additionally, there is the concern of having the adjacent lesions creating circumferential contracture of the pharynx at the tongue base level.

This application describes a modification of the FDA approved RFA procedure which addresses these issues and which can be performed in the office setting and the results of a case series review.

Subjects and Methods:

Consecutive cases from private practice were identified by computerized search using the electronic medical records software and CPT codes. Ninety-eight (98) records were identified. All 98 patient records were reviewed for complications and the number of procedures performed.

From the 98 patient records identified, patients were excluded who had any other procedure performed or any in the interval between pre- and post-VOAT PSG, and those who had not completed postoperative and preoperative PSG. This yielded 15 patients with PSG data before and after treatment with only the VOAT therapy. Information was reviewed for BMI before and after procedure, number of VOAT procedures and subjective data including ESS. All PSG data was reviewed to ensure the laboratory and reading physicians were using AASM criteria. Compiled results were subjected to Student's t-test. Institutional review board approval was obtained.

Operative Technique:

The operative technique is standardized as follows. Moderate sedation is induced with the assistance of a nurse anesthetist or anesthesiologist. The ventral aspect of the tongue is exposed by retracting the lower lip and jaw inferiorly and the tongue superiorly posteriorly. There is sufficient tension needed to spread out the mucosa over the under surface of the tongue and submandibular gland duct openings. The wand is used to puncture the mucosa about 5-10 mm superior to the submandibular gland duct openings in the midline. The wand is then slowly advanced in the midline sagittal plane along the midline fusion plane of the tongue. Advancing along the midline avoids aterio-venous and neural structure of the tongue. Base of tongue ablation was accomplished utilizing the ArthroCare Coblation Reflex 45 wand at a power level of 6 for 10 seconds and over a distance of 5-8 cm.

Results:

The average pre-operative AHI was 34.2 (standard deviation=23.8), post-operative average AHI of 9.98 (standard deviation =11.8). Student's t test results on pre and post-operative AHI data was significantly different with a p of 0.002. The average improvement in AHI was 24.34 or (72.3% improvement). 3 patients (20%) failed to improve significantly.

Overall complication rate 300 procedures reviewed showed 3 patients who required observation for bleeding and 1 patient with long term tongue tip numbness. There were no significant cases of dysphagia. There were no patients admitted for pain control.

Discussion:

The currently described VOAT modification shows significant reduction in apnea-hypopnea index (AHI) which averages 75% improvement in short term improvement, which compares favorably with previously reported data on the RFA BOT resulted in a 31% reduction in short term (<12 month) respiratory disturbance index (RDI) levels[6]. Although it compares favorably with previous reports, comparison using direct prospective data remains needed. From this data, one can reasonably conclude that VOAT is an improvement on the patient's untreated status.

Controlled study of treatment schemes for RFA suggests additional improvement in outcomes with repeated treatments [7]. This is likely to be seen with VOAT technique, but cannot be confirmed with the data available. Conclusions made regarding comparisons between the two techniques are also limited by small sample size in this current report. In addition, previous reports may have utilized a different generation of radiofrequency ablation hand piece, and therefore conclusions may suffer from type one error due to differences in equipment.

The current method for RFA BOT has some drawbacks which include possible bleeding from branches of the lingual vascular complex midline, which can cause swelling and potential airway problems. The vascular structures at this level cannot be identified readily from surface landmarks at this level.

Additionally, the lesions created by the current RFA BOT technique have a long axis of contracture and thus volume reduction is in a superior and inferior orientation. This theoretically results in less opening of the pharynx than if the lesions were anterior to posterior orientation. Hypothetically, there is the concern of having the adjacent lesions creating circumferential contracture of the pharynx at the tongue base level.

These risks of the current technique may be potentially alleviated by operating in the midline with the VOAT technique. The midline of the tongue has no significant neurovascular structures. Additionally, the lesions thus created by the ventral approach are along the axis of the geniohyoid and genioglossus and thus in an anterior and posterior orientation. This should hypothetically open the oropharynx and hypopharynx more than the current RFA BOT.

Complication rates from the VOAT study are comparable to reported complication rates in the literature for RFA BOT, 1% for this study compared with the published rate ranging from 1% to 4.6% [8, 9].

As noted above there is minimal morbidity with this procedure, as is true for current techniques for RFA BOT. Current FDA approved RFA commonly operates in the superior inferior plane. The VOAT lesions are arranged in an anterior to posterior plane, designed to improve suspension of the tongue and prevention of the tongue falling into the airway while the patient is supine. A prospective study with extended follow-up on RFA showed persistent improvements EDS and OSAS-QOL and median reaction time testing and apnea-hypopnea index [10]. Prior to concluding that VOAT is an improvement over the current technique, such data must be collected with the VOAT procedure The foregoing description of the exemplary embodiments has been presented only for the purposes of illustration and description and is not intended to be exhaustive or to limit the inventions to the precise forms disclosed. Many modifications and variations are possible in light of the above teaching.

The embodiments were chosen and described in order to explain the principles of the inventions and their practical application so as to enable others skilled in the art to utilize the inventions and various embodiments and with various modifications as are suited to the particular use contemplated. Alternative embodiments will become apparent to those skilled in the art to which the present inventions pertain without departing from their spirit and scope.

REFERENCES

[1] Gay P, Weaver T, Loube D, Iber C. Evaluation of positive airway pressure treatment for sleep related breathing disorders in adults. *Sleep.* 2006;29(3):381-401.

[2] Lindberg E, Berne C, Elmasry A, Hedner J, Janson C. CPAP treatment of a population-based sample—what are the benefits and the treatment compliance? *Sleep Medicine.* 2006;7(7):553-60.

[3] Maurer JT. Surgical treatment of obstructive sleep apnea: standard and emerging techniques. *Current Opinion Pulmonary Medicine.* 2010;16(6):552-8.

[4] Richard W, Timmer F, van Tinteren H, de Vries N. Complications of hyoid suspension in the treatment of obstructive sleep apnea syndrome. *European Archives of Otorhinolaryngology.* 2011; 268(4):631-5.

[5] Varghese R, Adams N G, Slocumb N L, Viozzi C F, Ramar K, Olson E J. Maxillomandibular advancement in the management of obstructive sleep apnea. *International Journal of Otolaryngology.* 2012;2012:373025.

[6] Farrar J, Ryan J, Oliver E, Gillespie M B. Radiofrequency ablation for the treatment of obstructive sleep apnea: a meta-analysis. Laryngoscope. 2008 October;118 (10):1878-83.

[7] Steward D L, Weaver E M, Woodson B T. Multilevel temperature-controlled radiofrequency for obstructive sleep apnea: extended follow-up. *Otol H&N Surg* 132(4): 630-5, 2005.

[8] Kezirian E J, Powell N B, Riley R W, Hester J E. Incidence of complications in radiofrequency treatment of the upper airway. *Laryngoscope* 2005; 115: 1298-1304.

[9] Toh S T, Hsu P P, Ng Y H, et al. Incidence of complications after temperature-controlled radiofrequency treatment for sleep-disordered breathing: a Singapore sleep centre experience. *J. Laryngol Otol* 2008 May; 122(5) :490-4.

[10] Ceylan K, Emir H, Kizilkaya Z, Tastan E, Yavanoglu A, Uzunkulaoglu H, Samim E, Felek SA. First-choice treatment in mild to moderate obstructive sleep apnea: single-stage, multilevel, temperature-controlled radiofrequency tissue volume reduction or nasal continuous positive airway pressure. *Arch Otolaryngol Head Neck Surg.* 2009 September;135(9):915-9.

What is claimed is:

1. A method for treating sleep apnea of a patient comprising:
    measuring a longitudinal thickness of a tongue of the patient between a proposed insertion point on a ventral surface of the tongue and a terminal point before inserting an electro-surgical instrument;
    determining an insertion depth of the electrosurgical instrument based on the measured longitudinal thickness,
    wherein the longitudinal thickness of the tongue is measured with a device comprising:
        an elongate measuring rod, the elongate measuring rod comprising linear distance measurement indicia;
        a spatula for placement on a dorsal surface of the tongue at the terminal point; and
        a sliding portion comprising an indicia marker and a stop region for placement at the proposed insertion point on the ventral surface of the tongue;
    wherein measuring comprises:
        placing the spatula portion in contact with the dorsal surface of the tongue at the terminal point; and
        sliding the stop region toward the spatula portion until the stop region contacts the ventral surface of the tongue,
    inserting a tip of an electro-surgical instrument at the insertion point on the ventral surface of the tongue of the patient;
    advancing the electro-surgical instrument toward the terminal point on the dorsal surface of the base of the tongue in a region proximate to the posterior pharyngeal wall;
    halting the advance of the tip of the electro-surgical instrument at a first distance from the terminal point;
    applying energy to tissue adjacent the tip of the electro-surgical instrument; and
    withdrawing the electro-surgical instrument while applying energy to tissue adjacent the tip of the electrosurgical instrument to create a lesion in the interior of the tongue, wherein creating the lesion results in contraction of a portion of the tongue which increases a distance between the base of the tongue and the posterior pharyngeal wall;
    wherein the lesion has a greater dimension in the anterior to posterior direction than in the superior to inferior direction.

2. The method of claim 1, wherein the electro-surgical instrument is an RF-energy ablation device.

3. The method of claim 1, wherein the electro-surgical instrument is a plasma assisted electrosurgical ablation device.

4. The method of claim 1, further comprising:
    ceasing the application of energy to the electro-surgical instrument at a second distance from the terminal point greater than the first distance prior to withdrawing the electro-surgical instrument.

5. The method of claim 1, wherein a stop is attached to the electro-surgical instrument, wherein the stop impedes insertion of the tip of the electro-surgical instrument beyond the first distance.

6. The method of claim 1, wherein the electro-surgical instrument includes:
    an adjustable stop selectively settable along a length of the electro-surgical instrument, wherein the stop impedes advancement of the tip of the electro-surgical instrument beyond the first distance; and
    linear indicia for indicating a distance between the tip of the electro-surgical instrument and the stop.

7. The method of claim 1, wherein the electro-surgical instrument is advanced along a sagittal line so as to avoid the ranine artery and the lingual nerve in the tongue.

8. The method of claim 1, wherein energy is applied to the electro-surgical instrument both during advancement and withdrawal of the instrument.

9. The method of claim 1, wherein the insertion point is 5-10 mm superior to the submandibular gland duct openings.

10. The method of claim 1, wherein the insertion point is within 10 mm of the midline sagittal plane of the tongue.

11. The method of claim 1, wherein a path of the electro-surgical instrument between the insertion point and the terminal point is within 10 mm of the midline sagittal plane of the tongue.

12. The method of claim 1, wherein the electro-surgical instrument comprises an elongate member having a distal and a proximal end, the instrument comprising at least one electrode adapted to apply electrical energy to tissue adjacent the proximal end of the tip.

13. The method of claim 1, wherein the first distance is 5-8 cm.

14. A method for use in ventral only ablation of a tongue of a subject, comprising the steps of:
    (a) providing an electrosurgical device comprising:
        (i) a retractor device for immobilizing the tongue in a connection with a ventral only ablation of the tongue procedure, comprising an elongate member comprising a proximal end and a distal end, the distal end of the elongate member angled downward to engage a dorsal surface of the base of the tongue;
        a handle adjacent the proximal end of the elongate member;
        a clamp adapted to slide along a first portion of the elongate member adjacent the handle;
        a retractor portion attached to and extending downwardly from the clamp, the retractor portion comprising a proximal portion attached to the clamp and a distal engaging portion adapted to engage a ventral undersurface of the tongue when the clamp is slid toward the distal end of the elongate member; and (ii) an elongate RF energy radiating member adapted for ventral insertion into the tongue from the ventral undersurface of the tongue, the RF radiating member having a proximal end and a distal end, the distal end radiating RF energy when inserted ventrally into the tongue;

and an adjustable stop selectively settable along a length of the elongate member for inhibiting further insertion of the elongate member upon contacting of the retractor portion of the retractor device when inserted into the ventral undersurface of the tongue;

(b) using the handle of the retractor device, placing the distal end of the elongate member against the dorsal surface of the base of the tongue of a subject;

(c) sliding the clamp of the retractor device along a first portion of the elongate member adjacent the handle to move the distal engaging portion to engage the ventral undersurface of the tongue of the subject, thereby immobilizing the tongue;

(d) setting a position of the adjustable stop of the RF energy radiating member to a desired predetermined insertion depth;

(e) inserting the distal end of the RF energy radiating member into the ventral undersurface of the tongue of the subject to the predetermined insertion depth; and (f) applying RF energy to the interior of the tongue of the subject to create a lesion on the interior of the tongue.

15. The method of claim 14, wherein the elongate RF radiating member further comprises:

linear indicia for indicating a distance between the adjustable stop and the distal end of the elongate member.

16. The method of claim 14, wherein the elongate RF energy radiating member comprises at least one electrode for delivering energy to tissue adjacent the distal end of the elongate member.

17. The method of claim 14, wherein the first portion of the elongate member includes linear measuring indicia, wherein the linear measuring indicia can be used to determine a distance between the distal end of the elongate member and the engaging portion of the retractor.

18. The method of claim 14, wherein the distal engaging portion of the retractor comprises a first curved member adapted to engage a first region adjacent to one side a midline sagittal plane of the tongue and a second curved member adapted to engage a second region adjacent the opposite side the midline sagittal plane of the tongue.

19. The method of claim 18, wherein the first and second curved members form a single continuous loop.

20. The method of claim 14, wherein the distal end of the elongate member comprises a flattened portion adapted to engage the dorsal surface of the base of the tongue.

21. The method of claim 14, wherein the elongate RF energy radiating member has a bend at a distance from the proximal end to form an angle of 5 to 30°.

22. The method of claim 21, wherein the distance is 2-6 cm.

* * * * *